United States Patent
Lautt et al.

(10) Patent No.: US 9,840,547 B2
(45) Date of Patent: Dec. 12, 2017

(54) HEPATIC INSULIN SENSITIZING SUBSTANCE AND TEST MEAL FOR INSULIN SENSITIZATION

(71) Applicant: SciMar Ltd., Gibsons (CA)

(72) Inventors: W. Wayne Lautt, Gibsons (CA); Helen Wang, Winnipeg (CA)

(73) Assignee: Scimar Ltd., British Columbia (CA)

( * ) Notice: Subject to any disclaimer, the term of this patent is extended or adjusted under 35 U.S.C. 154(b) by 0 days.

(21) Appl. No.: 14/277,365

(22) Filed: May 14, 2014

(65) Prior Publication Data

US 2014/0342981 A1 Nov. 20, 2014

Related U.S. Application Data

(60) Provisional application No. 61/823,068, filed on May 14, 2013.

(51) Int. Cl.
*C07K 14/62* (2006.01)
*A61K 38/28* (2006.01)
*G01N 33/66* (2006.01)
*G01N 33/74* (2006.01)
*C12Q 1/54* (2006.01)

(52) U.S. Cl.
CPC .............. *C07K 14/62* (2013.01); *A61K 38/28* (2013.01); *C12Q 1/54* (2013.01); *G01N 33/66* (2013.01); *G01N 33/74* (2013.01); *G01N 2333/62* (2013.01); *G01N 2800/042* (2013.01); *G01N 2800/044* (2013.01); *G01N 2800/32* (2013.01); *G01N 2800/347* (2013.01)

(58) Field of Classification Search
None
See application file for complete search history.

(56) References Cited

FOREIGN PATENT DOCUMENTS

| CN | 102845529 A | 1/2013 |
|---|---|---|
| DE | 10325797 A1 | 6/2003 |
| WO | 0213798 A2 | 2/2002 |
| WO | 2003061638 A2 | 7/2003 |
| WO | 2005019833 A1 | 3/2005 |

OTHER PUBLICATIONS

DeFronzo, "Pharmacologic Therapy for Type 2 Diabetes Mellitus," Amer. Coll. Phys. Amer. Soc. Int. Med. 131: 281-303 (1999).*
United Healthcare, diabetes, http://www.uhc.com/source4women/health_topics/diabetes/relatedinformation/d0f0417b073bf110VgnVCM1000002f10b10a_.htm—referenced Aug. 22, 2013.*
eMedicine Health, diabetes causes, http://www.onhealth.com/diabetes_health/page3.htm#diabetes_causes (referenced Aug. 22, 2013).*
Sansbury et al., "Regulation of obesity and insulin resistance by nitric oxide," Free Rad. Biol. Med. 73: 383-399 (2014).*
Wang et al., "A Synergistic, Balanced Antioxidant Cocktail, Protects Aging Rats from Insulin Resistance and Absence of Meal-Induced Insulin Sensitization (AMIS) Syndrome," Molecules 20:669-682 (published Jan. 2015).*
European Search Report for corresponding European Application 14168369 dated Oct. 22, 2014.
Santos, Celina et al. "In Vitro Nitrosatin of Insulin A- and B-chains", European Journal of Mass Spectrometry, IM Publications, US, vol. 12, No. 5, pp. 331-338 (Jan. 1, 2006).
Mikesh, L. M. et al. "The Utility of ETD Mass Spectrometry in Proteomic Analysis", Biochimica Et Biophysica Acta (BBA)—Proteins & Proteomics, Elsevier, Netherlands, vol. 1764, No. 12, pp. 1811-1822, (Dec. 1, 2006).
Lautt, W. Wayne et al. "Attenuation of Age-and Surose-Induced Insulin Resistance and Syndrome X by a Synergistic Antioxidant Cocktail: The AMIS Syndrome and HISS Hypothesis", Canadian Journal of Pysiology and Pharmacology, vol. 88, No. 3, pp. 313-323 (Mar. 1, 2010).
Lautt, W. Wayne et al. "HISS-Dependent Insulin Resistance (HDIR) in Aged Rats Is Associated With Adiposity, Progresses to Syndrome X, and Is Attenuated by a Unique Antioxidant Cocktail", Experimental Gerontology, 43, pp. 790-800 (2008).
Lautt, W. Wayne "A New Paradigm for Diabetes and Obesity: The Hepatic Insulin Sensitizing Substance (HISS) Hypothesis", Journal of Pharmacological Sciences, 95, pp. 9-17 (2004).
Chowdhury, K.K. et al. "Insulin Sensitization by Voluntary Exercise in Aging Rats Is Mediated Through Hepatic Insulin Sensitizing Substance (HISS)", Experimental Gerontology, Elsevier Science, Oxford, GB, vol. 46, No. 1, pp. 73-80 (Jan. 1, 2011).
Caperuto, Luciana Chagas et al. "Modulation of Bone Morphogenetic Protein-9 Expression and Processing by Insulin, Glucose, and Glucocorticoids: Possible Candidate for Hepatic Insulin-Sensitizing Substance", Endocrinology, 149 (12) pp. 6326-6334 (2008).
Foster, Matthew W. et al. "Protein S-Nitrosylation in Health and Disease: A Current Perspective", Trends in Molecular Medicine, Elsevier Current Trends, GB, vol. 15, No. 9, pp. 391-404 (Sep. 1, 2009).
Fernandes, A.B. et al. "Understanding Postprandial Glucose Clearance by Peripheral Organs: The Role of the Hepatic Parasympathetic System", Journal of Neuroendocrinology, 23, pp. 1288-1295 (2011).
Lautt, W. Wayne et al. "Rapid Insulin Sensitivity Test (RIST)", Can. J. Pharmacol. 76, pp. 1080-1086 (1998).
Lautt, W. Wayne et al. "Bethanechol and N-acetylcysteine Mimic Feeding Signals and Reverse Insulin Resistance in Fasted and Surcose-Induced Diabetic Rats", Can. J. Physiol. Pharmacol. 89, pp. 135-142 (2011).

(Continued)

*Primary Examiner* — Julie Ha
*Assistant Examiner* — Kristina M Hellman
(74) *Attorney, Agent, or Firm* — Thomas J. Engellenner; Reza Mollaaghababa Pepper Hamilton LLP

(57) ABSTRACT

The present invention provides methods of treating prediabetes, hyperglycemia, type 2 diabetes, AMIS syndrome, and obesity in a subject by administering to the patient HISS. The present invention also provides methods of diagnosing AMIS syndrome in a patient. Additionally, the present invention provides a method of shifting nutrient storage in meat-producing livestock to muscle rather than fat.

2 Claims, 10 Drawing Sheets

(56) References Cited

OTHER PUBLICATIONS

Patarrao, Rita S., "Meal-Induced Insulin Sensitization and Its Parasympathetic Regulation in Humans", Can. J. Physiol. Pharmacol. 86, pp. 880-888 (2008).

Seredycz, Larissa I. and Lautt, W. Wayne "Hemorrhage Results in Hepatic Insulin-Sensitizing Substance-Dependent Insulin Resistance Mediated by Somatostatin in Rats", Neuroendocrinology, 84 pp. 94-102 (2006).

Xie, Hongsheng et al., "Insulin Sensitivity Tested With a Modified Euglycemic Technique in Cats and Rats", Journal of Pharmacological and Toxicological Methods, 35 pp. 77-82 (1996).

Sadri, Parissa et al. "Fetal Ethanol Exposure Causes Hepatic Insulin Sensitizing Substance-dependent Insulin Resistance", Candian Journal of Diabetes, 27(3), pp. 239-247 (2003).

\* cited by examiner

HEPATIC INSULIN SENSITIZING SUBSTANCE AND TEST MEAL FOR INSULIN SENSITIZATION

FIELD OF INVENTION

The present invention relates generally to the diagnosis and treatment of metabolic disorders, and to pharmaceutical compounds which affect hyperglycemia, insulin resistance, Absence of Meal-Induced Insulin Sensitization (AMIS) syndrome, pre-diabetes, and diabetes.

BACKGROUND

AMIS syndrome describes a cluster of related pathologies that include obesity, diabetes, cardiovascular disease, retinal and kidney failure, and the metabolic dysfunctions associated with the originally-named Syndrome X. The original name of the syndrome and the subsequent 13 attempts to rename it, including the American Diabetes Association's renaming as Cardiometabolic Risk (CMR) (Grundy et al., 2005), did not determine a mechanistic link between the pathologies, other than as risk factors for other of the pathologies.

The suggestion to refer to this cluster of pathologies as the AMIS syndrome is based on the discovery of the phenomenon and mechanism of Meal-induced Insulin Sensitization (MIS), and how Absence of Meal-induced Insulin Sensitization (AMIS) results in the initiation of a progressive, predictable cluster of pathologies that are not diagnosed until well into the AMIS syndrome.

MIS is demonstrated by a much larger hypoglycemic response to insulin after a meal as compared with the response to insulin in the fasted state, as first reported in 2001 by the present inventor in rats (Lautt et al., 2001) and later confirmed by the present inventor in humans (Patarrao et al., 2008).

The degree of MIS is determined by the ability of pulses of insulin to cause the secretion of Hepatic Insulin Sensitizing Substance (HISS) from the liver. HISS is released from the liver in response to pulses of insulin, but only in the presence of 2 synergistic, permissive feeding signals, one neural via the hepatic parasympathetic nerves and one chemical through elevation of hepatic glutathione levels (Lautt et al., 2011). The nerve response is mediated by nitric oxide and cGMP. The feeding signals are activated by the presence of food in the upper GI tract, even if the food is a liquid injected into the stomach of anesthetized rats (Sadri et al., 2006). This knowledge of the biological role and signaling pathway of HISS is based on studies by the present inventor.

HISS more than doubles the hypoglycemic effect of insulin in rats (Lautt et al., 2001), and triples the effect in humans (Patarrao et al., 2008). The proportion of nutrient energy stored as glycogen or lipids is dependent on the balance between HISS and insulin. HISS acts by selective stimulation of glucose uptake and storage as glycogen in skeletal muscle, heart and kidneys, but not the liver, adipose tissue, or pancreas (Fernandez et al., 2011).

AMIS results in a reduction of at least 50% of the hypoglycemic response to secreted insulin for a single meal. AMIS occurs in states of stress (Seredycz et al., 2006). AMIS is induced by an isocaloric sucrose supplemented diet (Ribeiro et al., 2005), a high fat diet (Afonso et al., 2010), or fetal exposure to maternal consumption of alcohol (Sadri et al., 2003). AMIS occurs progressively with age (Lautt et al., 2008).

Glucose levels are well maintained despite AMIS, as long as increased insulin secretion can compensate for lack of HISS action. Increased insulin secretion almost fully compensates the resulting mild hyperglycemia after about 2 hours. Insulin, however, stimulates adipocytes and hepatocytes to form lipids for peripheral fat storage. The result is that in AMIS, where increased insulin secretion is necessary to compensate for lack of HISS action, nutrient storage after a meal shifts from glycogen to lipids. AMIS accounts for postprandial hyperglycemia, hyperinsulinemia and hyperlipidemia.

Alternatively, hyperglycemia can be controlled via the administration of insulin or cellular insulin sensitizers. However, this treatment is associated with adiposity since, as described above, insulin stimulates adipocytes and hepatocytes to form lipids for peripheral fat storage.

Direct insulin action is not altered by feeding (Sadri et al., 2006) so that the increased response to a bolus of insulin is not sensitized at the cellular level but rather at the whole body homeostatic level. Based on the in vivo bioassay procedure, invented by the present inventor in 1996 and used for cats and rats, and later for humans (Lautt et al., 2001), the biological activity of HISS has been well studied, and the pathologies of syndrome X have been shown to be strongly related to lack of HISS action, in the absence of altered direct insulin sensitivity (Xie et al., 2006).

AMIS is prevented and reversed in diabetic rats by voluntary exercise (Chowdhury et al., 2011). The present inventors developed a therapeutic that restores the response to each meal when the 2 feeding signals are mimicked (Lautt et al., 2011) and a targeted synergistic antioxidant cocktail that prevents or strongly inhibits the long term effects of a high sugar diet and aging (Lautt et al., 2010) by preservation of the ability of insulin to cause secretion of HISS.

The identification of the HISS compound is a novel discovery. Though two groups have previously claimed to identify HISS, neither identification was correct. A Hungarian team claimed that Somatostatin was HISS (Porszasz et al., 2003), however, somatostatin is actually a very effective blocker of HISS release and has no hypoglycemic action (Seredycz et al., 2006). A Brazilian team claimed that bone morphogenetic protein 9 was HISS (Caperuto et al., 2008), but the molecule has no rapid hypoglycemic effect and only acts after several hours. HISS, in contrast, is metabolized as quickly as insulin.

SUMMARY OF THE INVENTION

The present invention teaches an isolated peptide or protein comprising the amino sequence of SEQ ID NO:1 or an amino acid sequence having at least 70% or 80% or 90% identity therewith, the peptide or protein being nitrosylated at one or more of cysteine residues 7 and 19 of SEQ ID NO:1. In an embodiment, the peptide or protein is nitrosylated at cysteine residues 7 and 19 of SEQ ID NO:1. Pharmaceutical compositions comprising the isolated peptide or protein or a pharmaceutically acceptable salt thereof, and a pharmaceutically-acceptable carrier are also taught.

In an embodiment, the invention also teaches a method of treating or preventing one or more of hyperglycemia, pre-diabetes, Absence of Meal-induced Insulin Sensitization (AMIS) Syndrome, diabetes, a functional deficiency in Hepatic Insulin Sensitizing Substance (HISS), or a combination thereof in a mammal, the method comprising administering a therapeutically effective amount of the pharmaceutical composition of the invention. The invention also teaches a method of treating or preventing obesity or left ventricle cardiac weakness, or a combination thereof in a mammal, the method comprising administering a therapeutically effective amount of the pharmaceutical composition of the invention.

In an embodiment, the invention also teaches a method of shifting nutrient storage in a livestock animal from muscle to fat, the method comprising administering an effective amount of the pharmaceutical composition of the invention to the livestock animal.

In another embodiment, the invention teaches a method of determining a therapeutically effective dose of the pharmaceutical composition of the invention for administration to a mammal with hyperglycemia, the method comprising:
 (a) administering to the mammal the pharmaceutical composition of the invention at a test dosage;
 (b) feeding the mammal a standardized test meal;
 (c) obtaining a blood sample from the mammal;
 (d) assaying glucose levels in the blood sample; and
 (e) comparing the mammal's measured blood glucose levels to average healthy blood glucose levels for that mammal.

The methods of the invention may further comprise administering insulin to the mammal.

If the mammal's measured blood glucose level is greater than average healthy blood glucose levels for that mammal, the method of deteremining dosage may be repeated with the test dosage being increased by a pre-determined value. If the patient's measured blood glucose level is lower than average healthy blood glucose levels for that mammal, the method may be repeated with the test dosage being decreased by a pre-determined value.

In another embodiment is taught a test meal for use in diagnosing AMIS Syndrome or for determining a therapeutically effective dose of the pharmaceutical composition of the invention, the test meal comprising a soy milk base and a pre-defined amount of glucose. The pre-defined amount of glucose may be 1 g per kilogram of a test subject's body weight. The liquid test meal of the invention may have a pre-defined volume of 3⅓ ml per kilogram of a test subject's body weight.

The invention also teaches a method to assess Absence of Meal-induced Insulin Sensitization (AMIS) Syndrome, in a mammalian patient comprising:
 obtaining a fasted blood sample from the patient;
 feeding the patient;
 obtaining a fed blood sample;
 assaying levels of the isolated peptide or protein of the invention in the fasted and fed blood samples; and,
 determining the change in the levels of the isolated peptide or protein of the invention upon feeding.

DETAILED DESCRIPTION

Figure 1:
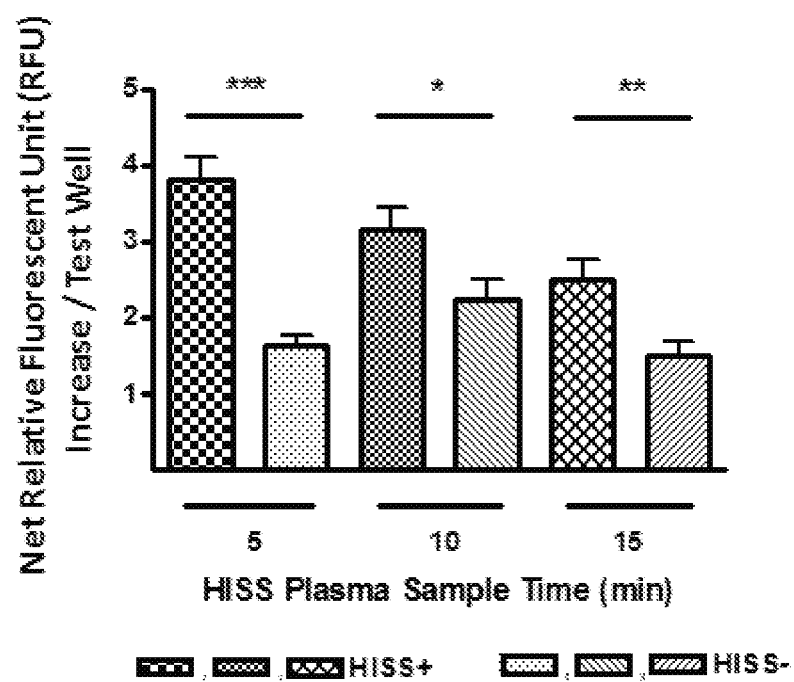
FIG. 1 is a graph showing HISS activity on glucose uptake in cultured L6 skeletal muscle cells.

The present invention is based on the discovery of the chemical structure of HISS. HISS is a 29 amino acid peptide (FVNQHLCGSHLVEALYLVCGERGFFYTPK) that is nitrosylated at cysteine residues 7 and 19 (See SEQ ID NO:1). The primary sequence of HISS is similar to the B chain of human insulin, however, the cysteine residues which would otherwise link the mature B chain of insulin to the A chain by disulfide bridges are modified by nitrosylation. The kinetics of insulin and HISS are similar. After an intravenous injection, the action of both hormones increases to a peak and returns to baseline after 35 min minutes in rats and 90 min in humans. HISS is stable for at least 24 hours at room temperature, and retains its activity even after being frozen and reconstituted from powder.

The present inventors have developed the following hypothesis. HISS is produced when insulin binds to receptors on the surface of the liver. The insulin is transported into the liver cells where it is acted upon by protein disulfide isomerase (PDI). PDI cleaves the insulin molecule into the A and B chain of insulin. Additional degradation of insulin occurs through the action of insulin degrading enzyme (IDE). Glutathione (GSH) is a peptide that serves a wide range of functions in the liver and cycles between the oxidized and reduced state. GSH activity influences the activity of PDI.

HISS may be used for treating hyperglycemia in a mammalian patient. It is believed that use of HISS to treat hyperglycemia spares the need for pancreatic secretion of insulin and therefore avoids the imbalanced nutrient storage after a meal as fat. Instead, since HISS is anabolic and glycogenic, nutrient storage after a meal is shifted to muscle, heart and kidneys. Addition of HISS to insulin administration can be used to mimic the normal healthy response to a meal and shift nutrient storage selectively to muscle, heart and kidneys. Alternatively HISS can be administered instead of insulin.

HISS may also be used for treating type 2 diabetes, AMIS syndrome and obesity in a patient suffering from a functional deficiency in HISS.

HISS may also be used in methods for diagnosing AMIS syndrome, even before insulin resistance, fasting hyperglycemia, adiposity, or elevated HBA1c occur.

Additionally, HISS has a positive anabolic effect on protein synthesis, and therefore it may be beneficial to administer HISS to meat-producing livestock to shift nutrient storage to muscle rather than fat.

HISS action may also prevent left ventricular cardiac weakness.

Pharmaceutical Compositions and Administration of HISS

There is provided a means of treating, or reducing the symptoms of conditions associated with insufficient HISS in a patient, comprising administering HISS or a pharmaceutically acceptable salt thereof to a patient. In many instances, it will be desirable to administer HISS together with insulin.

As used herein, the term "administering" to a subject includes dispensing, delivering or applying HISS, e.g., HISS in a pharmaceutical formulation (as described herein), to a subject by any suitable route for delivery of the compound to the desired location in the subject, including delivery by either the parenteral or oral route, intramuscular injection, subcutaneous/intradermal injection, intravenous injection, buccal administration, transdermal delivery and administration by the rectal, colonic, intranasal or respiratory tract route.

The present invention also provides pharmaceutically acceptable formulations comprising HISS. Such pharmaceutically acceptable formulations typically include HISS or a pharmaceutically acceptable salt thereof as well as a pharmaceutically acceptable carrier(s) and/or excipient(s). As used herein, "pharmaceutically acceptable carrier" includes any and all solvents, dispersion media, coatings, antibacterial and anti fungal agents, isotonic and absorption delaying agents, excipients and the like that are physiologically compatible. The use of such media and agents for pharmaceutically active substances is well known in the art. Except in so far as any conventional media or agent is incompatible with the HISS, use thereof in the pharmaceutical compositions is contemplated.

A pharmaceutical composition of the invention is formulated to be compatible with its intended route of administration. Examples of routes of administration include parenteral (e.g., intravenous, intradermal, subcutaneous), oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EI™ (BASF, Parsippany, N.J.) or phosphate buffered saline (PBS). In all cases, the pharmaceutical composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating HISS or a pharmaceutically acceptable salt thereof in the required amount in an appropriate solvent with one or a combination of the ingredients enumerated above, as required, followed by filtered sterilization. Generally, dispersions are prepared by incorporating the angiogenesis inhibitor compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of HISS or a pharmaceutically acceptable salt thereof plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, HISS or a pharmaceutically acceptable salt thereof can be incorporated with excipients and used in the form of tablets, troches, or capsules. Oral compositions can also include an enteric coating. Oral compositions can also be prepared using a fluid carrier for use as a mouthwash, wherein HISS or a pharmaceutically acceptable salt thereof in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the HISS or a pharmaceutically acceptable salt thereof is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the angiogenesis inhibitor compounds are formulated into ointments, salves, gels, or creams as generally known in the art.

HISS or a pharmaceutically acceptable salt thereof can also be prepared in the form of suppositories (e.g., with conventional suppository bases such as cocoa butter and other glycerides) or retention enemas for rectal delivery.

In one embodiment, HISS or a pharmaceutically acceptable salt thereof is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art.

HISS or a pharmaceutically acceptable salt thereof can also be incorporated into pharmaceutical compositions which allow for the sustained delivery of HISS or a pharmaceutically acceptable salt thereof to a subject for a period of at least several weeks to a month or more. Such formulations are described in U.S. Pat. No. 5,968,895.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of HISS or a pharmaceutically acceptable salt thereof calculated to produce the desired therapeutic effect in association with the required pharmaceutical carrier. The specification for the dosage unit forms of the invention are dictated by and directly dependent on the unique characteristics of HISS or the pharmaceutically acceptable salt thereof and the particular therapeutic effect to be achieved, and the limitations inherent in the art of compounding HISS or a pharmaceutically acceptable salt thereof for the treatment of individuals.

Therapeutic efficacy of HISS or a pharmaceutically acceptable salt thereof can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds of HISS or a pharmaceutically acceptable salt thereof which exhibit large therapeutic indices are preferred. The data obtained from the cell culture assays and animal studies can be used in formulating a range of dose for use in humans. The dose of HISS or a pharmaceutically acceptable salt thereof lies preferably within a range of circulating concentrations that include the ED50 with little or no toxicity. The dose may vary within this range depending upon the dosage form employed and the route of administration utilized. For any compounds of HISS or a pharmaceutically acceptable salt thereof used in the methods of the invention, the therapeutically effective dose can be estimated initially from cell culture assays. A dose may be formulated in animal models to achieve a circulating plasma concentration range that includes the IC50 (i.e., the concentration of HISS or a pharmaceutically acceptable salt thereof which achieves a half-maximal inhibition of symptoms) as determined in cell culture. Such information can be used to more accurately determine useful doses in humans. Levels in plasma may be measured, for example, by high performance liquid chromatography.

Example 1—In Vitro Confirming of HISS Identity

In vitro data confirmed the presence of HISS in plasma in fed rats (HISS+) in comparison with atropine HISS-blocked and fasting rats (HISS−), and demonstrated the peak HISS releasing time from the liver is at 5 min following insulin infusion (FIG. 1).

Plasma was collected from HISS+ (fed) and HISS− (fed with atropine blockage of hepatic muscarinic receptors; and fasting) anesthetized rats (n=34 total) at 5, 10 and 15 minutes after the initiation of a 5 minute 100 mU/kg bolus insulin intravenous infusion. This time was chosen since insulin levels decrease to baseline in plasma within 5 minutes, however, the in vivo hypoglycemic response peaks at 15-20 minutes (Lautt et al., 2001) due to HISS action. HISS action is delayed by about 4 minutes, and peaks at 19 minutes in rats and 40 minutes in humans.

Plasma HISS activity on glucose uptake was tested in cultured L6 skeletal muscle cells using optimal assay conditions ($3.06 \times 10^3$ cells/well/6-well plate, 8-day full growth cycle, no starvation, final 6% plasma/DMEM, 45 min stimulation at 37° C. with 2-3 washes in PBS) using fluorescent glucose analog, 2-(N-(7-nitrobenz-2-oxa-1,3-diazol-4-yl) amino)-2-deoxyglucose (2-NBDG, 0.22 mM), as an indicator (excitation/emission, 467/542 nm). The net relative fluorescence unit (RFU) increase/test well was calculated by subtracting background RFU value in the control well (L6 cells+DMEM+2NBDG-HISS plasma/plate). Individual plasma samples were tested in 1-3 wells/sample with 2 measurements/well. Data were obtained from 19 culture plates from 11 experiments, and expressed as Mean±SE. *: $P<0.05$; : $P<0.01$; *: $P<0.0001$, unpaired t tests.

Example 2—Identifying the Activity of HISS

The observed half-lives of HISS activity in vitro of 14.4 min (FIG. 2) and 8.2 min in vivo (FIG. 3) suggest a rapid clearance of this hormone by the tissues upon which it acts, with a slightly longer duration when tested in vitro than in vivo.

Figure 2:
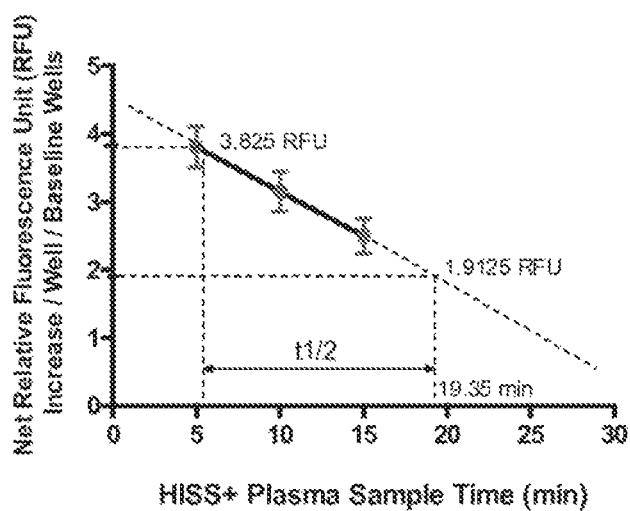
FIG. 2 is a graph showing the half-life of HISS activity when tested in vitro in cultured L6 skeletal muscle cells.

FIG. 2 is a linear graph of the data from FIG. 1 using HISS+ plasma samples (n=17 rats), demonstrating the kinetics of HISS glucose uptake activity decrease in plasma between 5-15 min of sample time. A half-life of 14.35 min arose when HISS+ plasma samples were tested in vitro in cultured L6 skeletal muscle cells.

Figure 3:
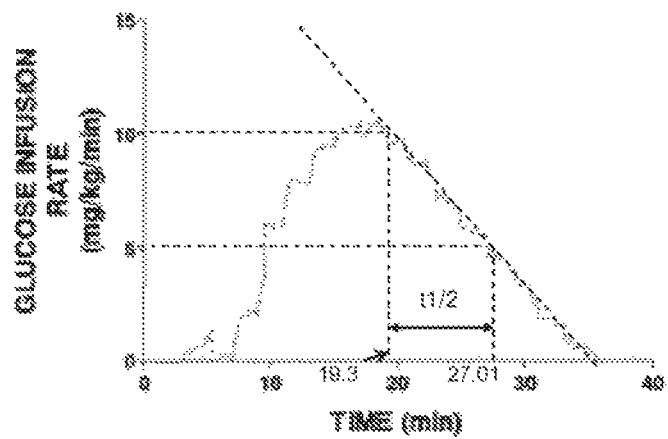
FIG. 3 is a graph showing the half-life of HISS activity in vivo.

FIG. 3 shows the decrease in HISS activity in stimulating glucose uptake in body cells in vivo. The half-life of HISS activity was 8.21 min. This was calculated from an extrapolated slope of HISS effects on a glucose infusion profile curve using a euglycemic clamp (Lautt et al., 2001) following the rapid insulin sensitivity test (RIST) procedure as described in the literature (Lautt et al., 1998). Briefly, the RIST procedure involves a transient euglycemic clamp in response to a bolus administration of 50 mU/kg insulin. Euglycemia is maintained by infusion of glucose throughout the 35-minute period of insulin action. The RIST index is the amount of glucose that was required in order to prevent blood glucose levels from declining in response to insulin. Baseline glycemia is established by comparison of glucose levels in blood taken at 5-minute intervals. The average of these stable glycemic values is used as the target glycemia to maintain throughout the RIST. Insulin is administered by constant infusion over a 5-minute period and blood glucose levels are sampled after the first minute of insulin administration and at 2-minute intervals thereafter with glucose levels being maintained at the target baseline through use of a variable glucose infusion. Typically the glucose infusion rate must be increased to a peak level between 15 and 20 minutes and no further glucose is required after 35 minutes from the onset of insulin administration. The total amount of glucose required to prevent hypoglycemia is referred to as the RIST index and is expressed as mg glucose/kg body weight.

Example 3—Identifying HISS as Distinct from Insulin

Data show glucose uptake stimulated in cultured skeletal muscle cells is due to HISS action but not insulin (FIGS. 4 & 5), suggesting HISS is distinct from insulin.

Figure 4:
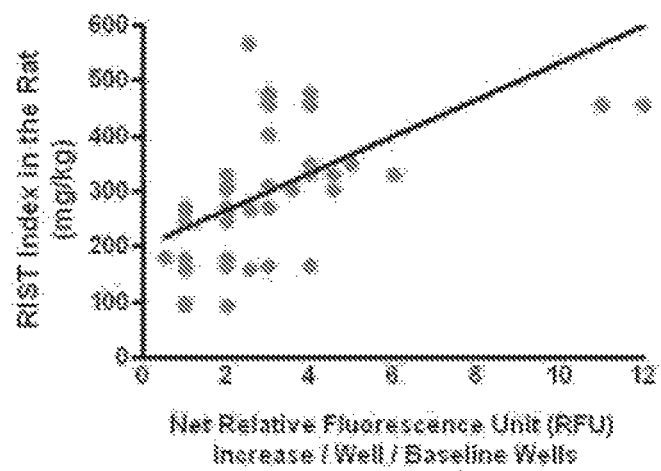
FIG. 4 is a graph showing the correlation between the in vivo RIST index and the in vitro L6 skeletal muscle cell glucose uptake.

FIG. 4 shows the correlation between RIST index and RFU. The in vivo RIST index and in vitro L6 skeletal muscle cell glucose uptake, as represented by RFU, stimulated by the same HISS+/− plasma samples were plotted and analyzed by linear regression analysis. Increased RIST index correlated with increased glucose uptake in cultured L6 cells (overlapping data points invisible).

Figure 5:
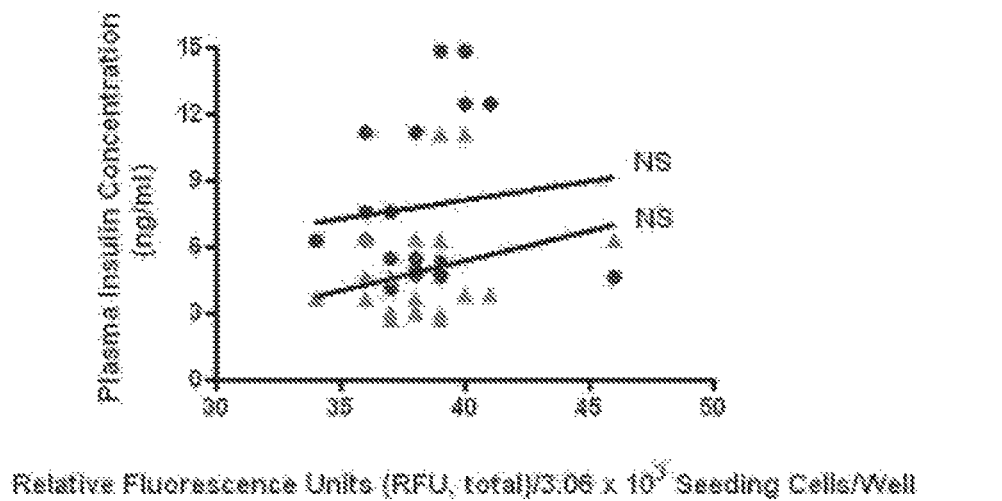
FIG. 5 is a graph showing the correlation between plasma insulin concentration and glucose uptake measured by relative fluorescence.

FIG. 5 shows the correlation between plasma insulin concentration and RFU. Plasma insulin concentrations were quantified by ELISA using samples taken at 4 min 45 sec and 5 min of insulin infusion in the same rat. Individual insulin concentrations were plotted with glucose uptake response RFU in cultured L6 skeletal muscle cells stimulated by plasma from the same rats, and analyzed by linear regression analysis.

The data show no correlation between insulin concentration and RFU in the bioassay, demonstrating the glucose uptake response in L6 cells was not stimulated by insulin but instead, by HISS (overlapping data points invisible).

Example 4—Identifying the Stability of HISS

Figure 6:
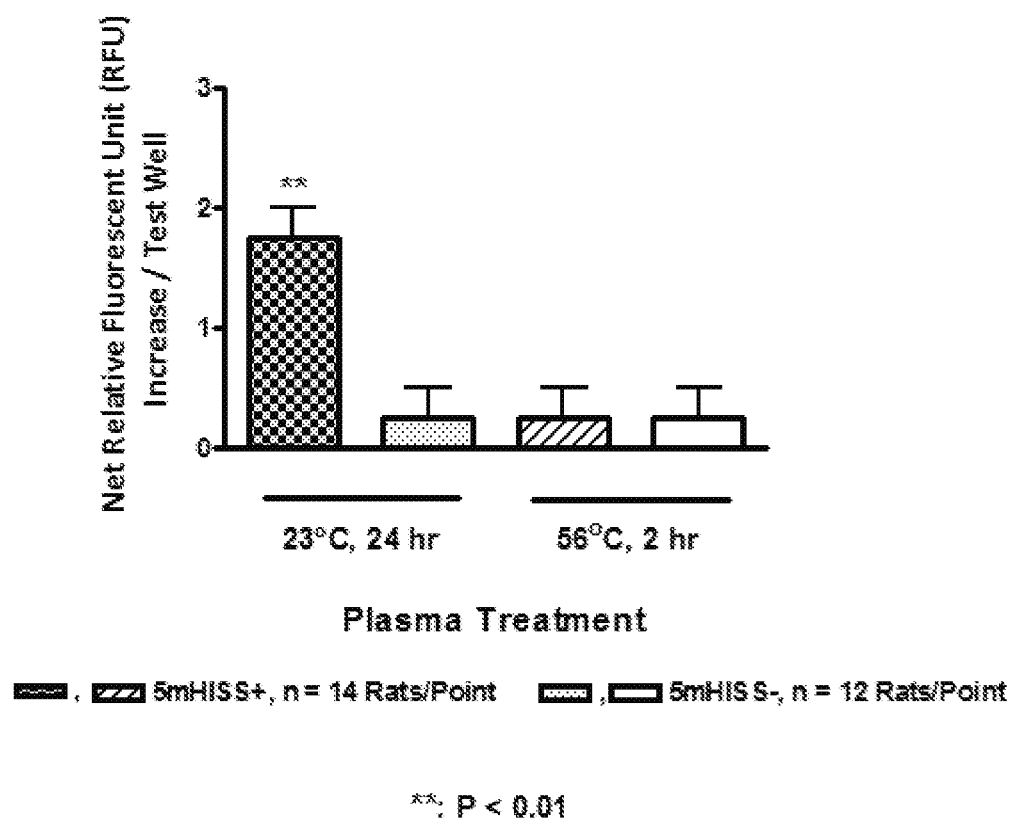
FIG. 6 is a graph showing the stability of HISS activity after treatment at 56° C. for 2 hr and at room temperature (23° C.) for 24 hr.

HISS was shown to be stable at room temperature for at least 24 hr, but activity was destroyed at 56° C. for 2 hr, demonstrating it is of protein in nature and suitable for clinical laboratory testing (FIG. 6).

FIG. 6 shows the results of a HISS activity stability test. Plasma was collected at 5 min of insulin infusion from HISS+/− rats (n=26 total), pooled, divided and treated at 56° C. for 2 hr and at room temperature (23° C.) for 24 hr. Treated plasma was immediately tested in bioassay at the end of each treatment using optimal conditions. Data were obtained from 2 wells/pooled plasma group, 2 measurements/well, 4 culture plates, 2 experiments, and expressed as Mean±SE. **: $P<0.01$, unpaired t test.

Results show HISS activity is stable at room temperature but destroyed at 56° C. demonstrating the protein nature of HISS molecule.

Example 5—Identifying the Molecular Weight of HISS

Figure 7:
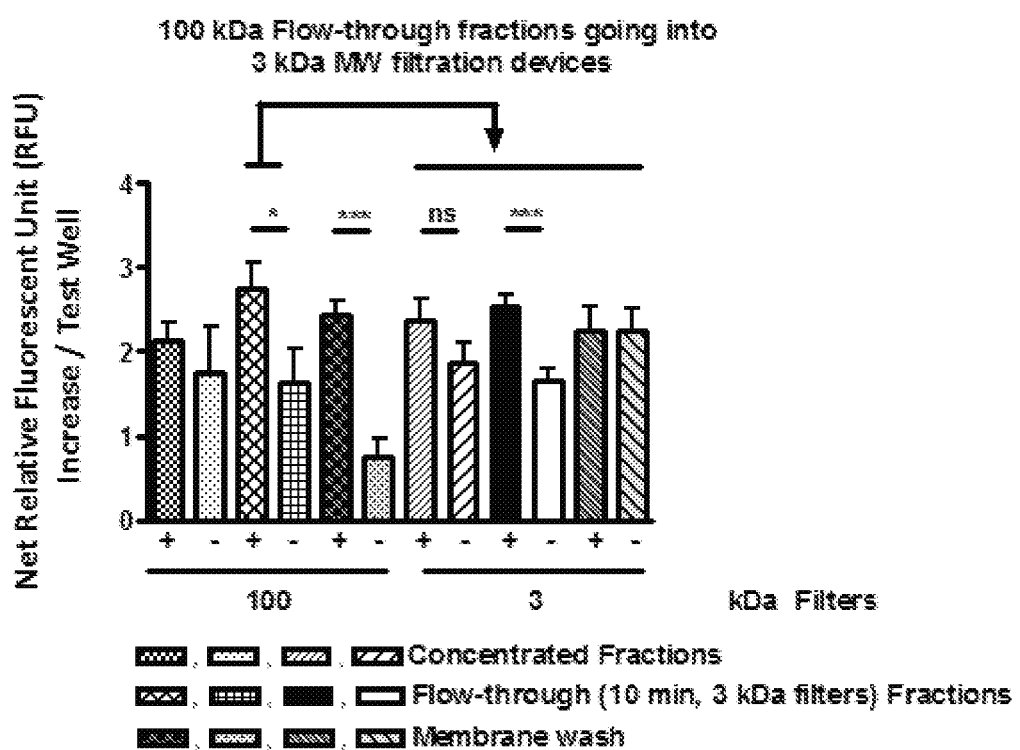
FIG. 7 is a graph showing HISS plasma serial molecular weight (MW) filtration.

The molecular weight of HISS was demonstrated to be around 3000 Da (FIG. 7).

FIG. 7 shows pooled HISS plasma serial molecular weight (MW) filtration. HISS+/− plasma collected at 5 min of insulin infusion was pooled (n=9-13 rats/HISS+ group, n=9-12 rats/HISS− group), and filtered through 100 kDa MW filtration centrifugal devices using optimal conditions (no prerinse, 1.2 ml plasma/tube, 3500 g, 1 h 15 m, 4° C.). The 100 kDa flow-through fraction went into the $2^{nd}$ filtration by 3 kDa MW filtration centrifugal devices using optimal conditions (no prerinse, 1.2 ml/tube, 3000 g, 10, 30 and 60 min, 4° C.). The flow-through and concentrated fractions, and membrane washes (1 membrane/2 ml DMEM/well, overnight wash, room temperature, 6% in assay) from both 100 and 3 kDa MW filtration were tested in optimal bioassay conditions for HISS activity on stimulation of glucose uptake in cultured L6 cells. Data were combined from 8 Serial MW filtration runs, 4-13 wells/group, 2 measurements/well, 27 culture plates, 11 experiments, and expressed as Mean±SE. *: $P<0.05$; ***: $P<0.0001$, unpaired t tests.

The high HISS activity present in the 10 min flow-through fraction of 3 kDa MW filters demonstrates HISS molecular weight being around 3 kDa.

Example 6—Confirming HISS Identity by Mass Spectrometry

HISS was sequenced and found to be a peptide of 29 amino acids, FVNQHLCGSHLVEALYL-VCGERGFFYTPK.

Example 7—Identifying Features of HISS

Figure 8:
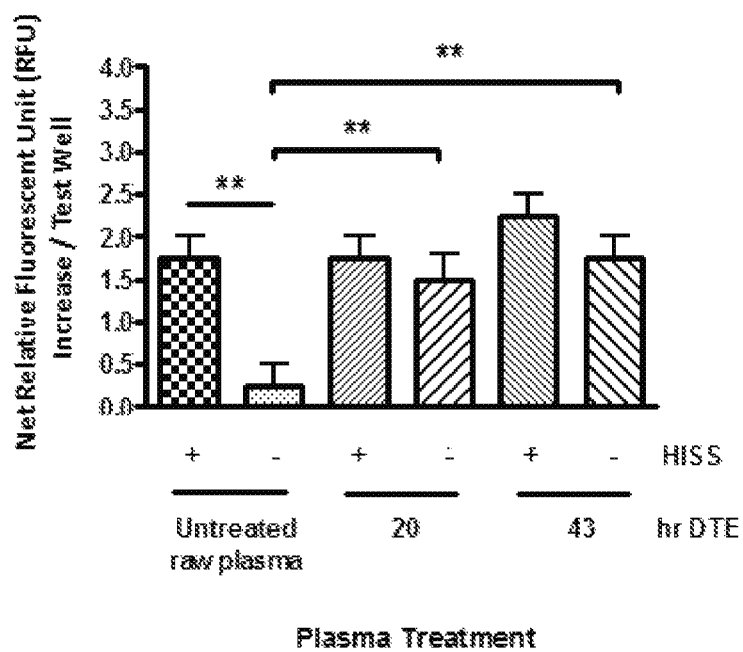
FIG. 8 is a graph showing Dithioerythritol (DTE) reduction of HISS.

HISS was demonstrated to contain at least one disulfide bond (FIG. 8). Opening disulfide bond(s) can cause increased HISS activity, implying HISS activity is directly linked with modification on sulfur (S) atom(s) of the cysteine residue(s) in HISS molecule (FIG. 8).

FIG. 8 shows dithioerythritol (DTE) reduction of HISS+/− plasma. Individual HISS+(fed) and HISS− (fasting) rat plasma was collected at 5 min following insulin infusion, treated with DTE at 1.25 mM final concentration for 20-43 hr at room temperature, and tested for HISS activity in the bioassay immediately after treatment (N=2-5 wells/group, 2 measurements/well, 5 culture plates, 2 experiments). Data are expressed as Mean±SE. **: $P<0.01$, unpaired t tests.

DTE plasma reduction results demonstrated that HISS molecule contains at least one disulfide bond and breaking the —S—S— bond(s) is associated with altered HISS activity, further confirming the protein structural feature of HISS molecule.

Example 8—Identifying Nitrosylation of HISS

Figure 9:
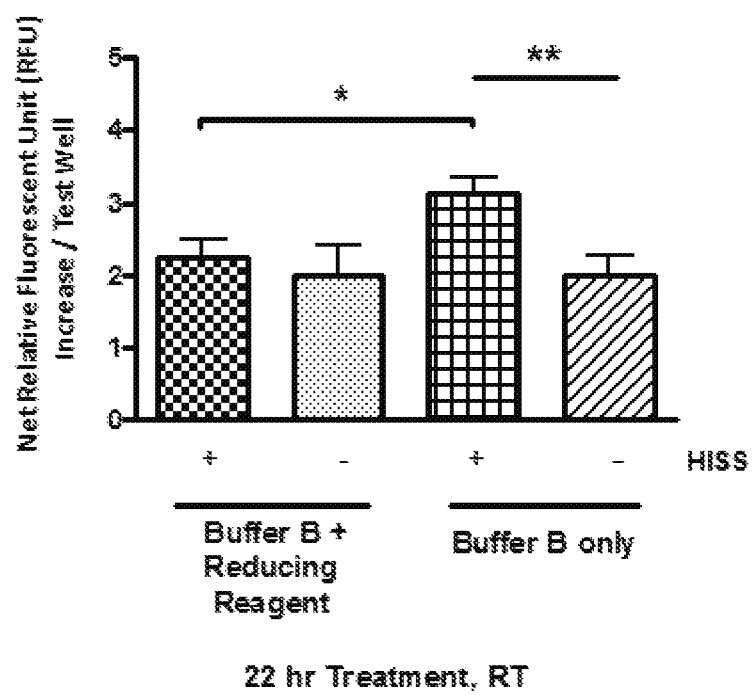
FIG. 9 is a graph showing S-Nitrosylation kit reduction of HISS.

The post translational modification on HISS molecule was shown to be nitrosylation (FIG. 9). Removal of the NO group leads to decreased HISS activity (FIG. 9).

FIG. 9 shows S-Nitrosylation kit reduction of HISS+/− plasma. Pooled 5 min HISS+ (n=6-8 rats) and HISS− (n=5-7 rats) plasma samples were treated with partial S-Nitrosylated Protein Detection Assay kit (Cayman Chemical Company) at room temperature (RT) to reduce (remove) NO group from the S—NO moiety (S-nitrosylation), and test the hypothesis that HISS is a nitrosylated protein. Reduced plasma was tested in bioassay immediately at the end of treatment. Data from 22 hr treatment time were collected from n=2-4 wells/group, 2 measurements/well, 3 culture plates, 2 experiments, and expressed as Mean±SE. *: $P<0.05$; **: $P<0.01$; unpaired t tests.

Results showed significantly decreased HISS activity in reduced plasma in comparison with non-reduced controls, demonstrating nitrosylation is present in HISS molecule and plays a critical role in HISS glucose uptake activity.

Example 9—Efficacy of HISS

Figure 10:
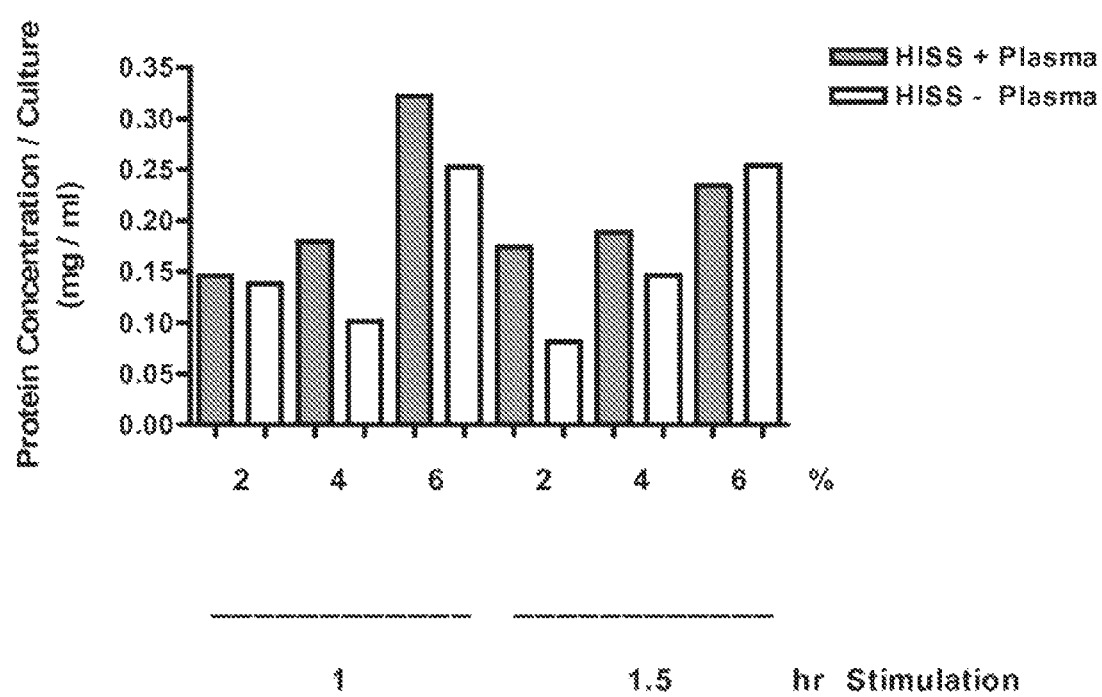
FIG. 10 is a graph showing cultured L6 cell protein content change under HISS stimulation.

Experiments demonstrated increased protein synthesis in cultured skeletal muscle cells under the stimulation of HISS+ plasma at various concentrations tested (FIG. 10).

FIG. 10 shows cultured L6 cell protein content change under HISS+/− plasma stimulation. Optimal growth conditions were used (3.06×10³ cells/well/6-well plate, 8-day full growth cycle) with 4 hr cell starvation in DMEM culture medium only, and final 2, 4 and 6% HISS+/− plasma plus 5.55 mM glucose added as supplement per well for 1 and 1.5 hr stimulation time at 37° C. L6 cells were harvested by 1 wash with 2 ml PBS/well, lysed with 0.5 ml 0.1 N NaOH/well and stored at −80° C. prior to protein quantification assay using Bio-Rad Protein Assay Standard Procedure. Data were collected from pooled 3 wells/sample from the same experiment.

Results showed steady protein content increase with increased HISS+ plasma concentrations/well at both 1 and 1.5 hr stimulation time points, with background protein content increasing in the same trend but to lower levels in HISS− plasma stimulated wells.

Example 10—Preparing a Test Meal for Determining a Therapeutically Effective Dose of HISS or for Diagnosing AMIS Syndrome A suitable test meal for determining a therapeutically effective dose of HISS or for diagnosing AMIS Syndrome will have a soy milk base, a pre-defined amount of glucose, and optionally, flavouring.

Soy milk has an appropriate combination of lipids, carbohydrate and protein to activate the feeding signals which allow insulin to stimulate HISS release. In contrast, a test meal consisting of only sucrose or glucose, such as those commonly used in an oral glucose tolerance test, will not activate these feeding signals. Another limitation with a normal mixed meal is that the glucose elevation after a mixed meal is not sufficiently large for simple finger-prick blood glucose determinations to be useful as a sensitive indicator of glucose storing capacity. Soy milk therefore offers a convenient alternative to a mixed meal comprised of a wide range and combination of foods. The soy milk base can be provided in liquid or dried powder form.

Glucose is then added to the soy milk base to create a high sugar load, which will result in larger hyperglycemic excursion than a normal mixed meal. Glucose by itself will not stimulate HISS release; however, a test meal according to the present invention stimulates both insulin and HISS release.

Maintaining a standard dosage of glucose and soy milk is important for achieving standardized results between test subjects. The oral glucose tolerance test is given at the same dose for every body size, thus complicating comparisons of the degree of postrprandial hyperglycemia.

In the present invention, the test meal is adjusted based on the subject's body weight. For example, soy milk can be provided at 3⅓ ml per kilogram of body mass (i.e. 250 ml for an average 75 kg subject). Glucose can then be added at a dosage of 1 gram per kilogram of body mass (i.e. 75 grams for an average 75 kg subject). The volume of the test meal is therefore adjusted according to body weight, as is its glucose content. In some embodiments, the test meal is packaged in or with a container that includes calibrated markings which allow the user to determine the appropriate volume based on the subject's body mass.

A test meal provided in liquid form is easier for many subjects to consume than other alternatives, such as dried oat biscuits marketed by Cepro™ in Edmonton, Alberta. A liquid meal is often consumed more quickly by subjects and absorbed more rapidly than a dry meal, both of which improves standardization. In addition, a test meal consisting of pure glucose (such as the test meal used in the oral glucose tolerance test) often causes nausea. A liquid soy-based test meal, particularly one with flavouring, may be perceived by subjects as less unusual and therefore may be better tolerated. Liquid meals can also be easier to prepare in terms of standardizing the dosage and volume of the mean based on the subject's body mass.

Accordingly, the test meal may be designed to be reconstituted in water, pre-packaged as a liquid meal, or provided as a liquid soy milk base along with glucose to be added to a pre-defined volume of soy milk based on body weight.

Example 11—Calculating an Appropriate Dose of HISS as a Therapeutic

The dose of HISS or a pharmaceutically acceptable salt thereof to be administered can be estimated based on the dose of insulin that is being replaced. The appropriateness of the dose administered can be verified by showing improvement in a patient's glucose levels, evaluated exactly as insulin dose is verified and adjusted according to need.

HISS or a pharmaceutically acceptable salt thereof and a pharmaceutically-acceptable carrier, and optionally insulin, is administered to the patient based on his/her clinical condition and sensitivity to insulin. Response to the test meal may be used as an additional means of evaluating effective dosage. The patient drinks a standardized test meal according to Example 10 above.

Next, a blood sample should be taken from the patient and the glucose levels in the sample assayed. Finally, the patient's measured blood glucose levels should be compared to average healthy blood glucose levels.

If the patient's measured blood glucose level is greater than average healthy blood glucose levels, the method is repeated with the amount of HISS or a pharmaceutically acceptable salt thereof administered being increased. If the patient's measured blood glucose level is lower than average healthy blood glucose levels, the method is repeated with the amount of HISS or a pharmaceutically acceptable salt thereof administered being decreased.

Example 12—Use of HISS as a Diagnostic

A HISS assay can be used to diagnose AMIS and detect the AMIS syndrome well before insulin resistance, fasting hyperglycemia, adiposity, or elevated HBA1c occurs.

To diagnose AMIS syndrome in a human subject, a fasted plasma sample is obtained from the patient. Next the patient is fed with a standardized test meal according to Example 10 above, and fed plasma samples are obtained from the patient at one or more time points up to about 120 minutes after the standardized test meal is eaten. HISS levels, and optionally insulin and/or glucose levels, are assayed in the fasted and fed plasma samples, and the change in these levels upon feeding is determined.

If only one fed plasma sample is taken, it should be taken at about 20 minutes to about 45 minutes after the standardized test meal is eaten as this window is best to detect increases in HISS, insulin and glucose.

If two or more fed plasma samples are taken, at least one fed plasma sample should be taken at about 20 to about 45 minutes after the standardized test meal is eaten and at least one other fed plasma sample should be taken at about 90 minutes to about 120 minutes after the standardized test meal is eaten. The 90 to 120 minute window provides valuable additional data, as a healthy response will show a return toward baseline for all 3 parameters by this time.

The HISS, and optionally insulin and/or glucose levels, in both the fasted and fed plasma samples can be compared to average healthy values or with the subject's own past test results to evaluate interventions including diet, physical training, pharmaceuticals, nutraceuticals, alternative medical programs or lifestyle.

Example 13—Use of HISS as a Diagnostic

The following alternate HISS assay can be used to diagnose AMIS and detect the AMIS syndrome well before insulin resistance, fasting hyperglycemia, adiposity, or elevated HBA1c occurs.

After a 24 hour fast, or other lesser but standardized time, a bolus intravenous insulin injection of 50 mU/Kg is administered to the subject, and the euglycemic clamp/RIST procedure (Patarrao et al., 2008) is used to detect direct insulin action in the fasted state. The RIST index obtained is the amount of glucose required to maintain a steady baseline glucose level after insulin administration. The patient consumes the standard test meal described in Example 10 above, and 90 minutes afterwards another bolus intravenous insulin injection of 50 mU/Kg is administered to the subject and the euglycemic clamp/RIST procedure is again used to detect direct insulin action, this time in the fed state.

Comparison of the responses in the fasted and fed state allows for calculation of the degree of MIS.

Although the invention has been described with reference to illustrative embodiments, it is understood that the invention is not limited to these precise embodiments and that various changes and modifications may be effected therein by one skilled in the art. All such changes and modifications are intended to be encompassed in the appended claims.

REFERENCES

Afonso et al., 2010 Br. J. Nutr. 104 1450-1459
Caperuto et al., 2008 Endocrinology 149(12): 6326-35
Chowdhury et al., 2011 Exp. Gerontol 46: 73-80 (202)
Fernandes et al., 2011 *J. Neuroendocrinol.* 23(12): 1288-1295
Grundy et al., 2005 Circulation 112 2735-2752 (pmid 16157765)
Lautt et al., 1998 Can. J. Physiol. Pharmacol. 76:1080-1086
Lautt et al., 2001 Am J Physiol. 281:G29-G36 (152)
Lautt et al., 2008 Exp. Gerontol. 43:790-800 (191)
Lautt et al., 2010 Can J. Physiol. Pharmacol. 88:313-323. (195)
Lautt et al., 2011 Can. J. Physiol. Pharmacol. 89:135-142. (200)
Patarrao et al., 2008 Can. J. Physiol. Pharmacol. 86, 880-888. (192)
Porszasz et al., 2003 *Br J. Pharmacol.* 139(6):1171-9
Ribeiro et al., 2005 Diabetologia 48: 976-983 (173)
Sadri et al., 2003 Can. J Diabetes 27:239-247 (164)
Sadri et al., 2006 Br. J. Nutr. 95:288-295 (179)
Seredycz et al., 2006 Neuroendocrinology 84:94-102 (183)
Xie et al., 2006 J. Pharmacol. Toxicol. Meth. 35: 77-82 (116)

---

We claim:

1. A pharmaceutical composition comprising:

an isolated peptide or protein consisting of the amino acid sequence of SEQ ID NO: 2 or an amino acid sequence having at least 90% identity therewith, wherein said peptide or protein is nitrosylated at one or more of cysteine residues 7 and 19 of SEQ ID NO: 2, or a pharmaceutically acceptable salt and a pharmaceutically acceptable carrier thereof; and wherein the pharmaceutically acceptable carrier is selected from the group consisting of bacteriostatic water, phosphate buffered saline, ethanol, a polyol, microcrystalline cellulose, gelatin, magnesium stearate, synthetic solvents, ethylene vinyl acetate, polyanhydrides, polyglycolic acid, polyorthoesters, polylactic acid and a combination thereof.

2. The pharmaceutical composition of claim 1, wherein said peptide or protein is nitrosylated at cysteine residues 7 and 19 of SEQ ID NO: 2.

* * * * *

SEQUENCE LISTING

```
<160> NUMBER OF SEQ ID NOS: 4

<210> SEQ ID NO 1
<211> LENGTH: 29
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Nitrosylated Cys Residue
<220> FEATURE:
<221> NAME/KEY: MOD_RES
<222> LOCATION: (19)..(19)
<223> OTHER INFORMATION: Nitrosylated Cys Residue

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 2
<211> LENGTH: 29
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25
```

```
<210> SEQ ID NO 3
<211> LENGTH: 29
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Nitrosylated Cys Residue

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 4
<211> LENGTH: 29
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Nitrosylated Cys Residue

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25
```